(12) United States Patent
Van Dooren et al.

(10) Patent No.: US 6,287,799 B1
(45) Date of Patent: Sep. 11, 2001

(54) PROCESS FOR THE PREPARATION OF A β-LACTAM ANTIBIOTIC

(75) Inventors: Theodorus Johannes Godfried Marie Van Dooren, Roermond (NL); Johanna Christina Maria Smeets, North Attleboro, MA (US); Harold Monro Moody, Maastricht (NL)

(73) Assignee: DSM N.V. (NL)

( * ) Notice: Subject to any disclaimer, the term of this patent is extended or adjusted under 35 U.S.C. 154(b) by 0 days.

(21) Appl. No.: 09/529,569

(22) PCT Filed: Oct. 1, 1998

(86) PCT No.: PCT/NL98/00570

§ 371 Date: Apr. 18, 2000

§ 102(e) Date: Apr. 18, 2000

(87) PCT Pub. No.: WO99/20786

PCT Pub. Date: Apr. 29, 1999

(30) Foreign Application Priority Data

Oct. 17, 1997 (NL) .................................................... 1007302

(51) Int. Cl.$^7$ .............................. C12P 35/04; C12P 37/04
(52) U.S. Cl. ................. 435/43; 435/41; 435/50; 435/177; 435/178; 435/180
(58) Field of Search .......................................... 435/43, 41

(56) References Cited

FOREIGN PATENT DOCUMENTS

| 9201061 | 1/1992 | (WO) . |
| 9602663 | 2/1996 | (WO) . |
| 9623897 | 8/1996 | (WO) . |
| 9722610 | 6/1997 | (WO) . |

*Primary Examiner*—Francisco Prats
*Assistant Examiner*—Brett Ozga
(74) *Attorney, Agent, or Firm*—Bierman, Muserlian and Lucas

(57) ABSTRACT

Process for the preparation of a β-lactam antibiotic in which a β-lactam nucleus is subjected to an enzymatic acylation reaction with the aid of an acylation agent at a molar ratio of acylation agent/β-lactam nucleus of less than 2.5, with the acylation agent and/or the β-lactam nucleus being supersaturated in the reaction mixture during at least part of the acylation reaction. In the process, a concentrated slurry or solution, for instance, of the β-lactam nucleus and/or the acylation agent with a different pH or a higher temperature than the pH or temperature at which the acylation reaction is carried out is added to the reaction mixture during the acylation reaction. Both the β-lactam nucleus and the acylation agent may be supersaturated in the reaction mixture.

16 Claims, No Drawings

PROCESS FOR THE PREPARATION OF A β-LACTAM ANTIBIOTIC

This application is a 371 of PCT/NL98/00570 filed Oct. 1, 1998.

The invention relates to a process for the preparation of a β-lactam antibiotic in which a β-lactam nucleus is subjected to an enzymatic acylation reaction with the aid of an acylation agent at a molar ratio of acylation agent/β-lactam nucleus of less than 2.5.

A similar process is disclosed in for example WO-A-96/23897.

The yield of β-lactam antibiotic to be achieved in the enzymatic acylation reaction according to the prior art per amount of β-lactam nucleus employed and per amount of acylation agent employed is in general relatively low inasmuch as the β-lactam nuclei and/or the β-lactam antibiotics often are relatively instable, whilst the reaction time is relatively long because of the usually low solubility of the reactants. Moreover, at the relatively low acylation agent to β-lactam nucleus ratio mentioned, only a relatively low yield of β-lactam antibiotic can be achieved per amount of β-lactam nucleus employed.

The invention provides a process in which in an enzymatic acylation reaction a shorter reaction time is achieved and a higher yield of β-lactam antibiotic is achieved per amount of β-lactam nucleus and/or per amount of acylation agent employed, with the ratio of the amount of acylation agent employed to β-lactam nucleus being relatively low.

This is achieved according to the invention in that the acylation agent and/or the β-lactam nucleus are/is supersaturated in the reaction mixture during at least part of the acylation reaction.

The applicant has found that it is possible to achieve a high degree of supersaturation of the β-lactam nucleus and/or the acylation agent in the reaction mixture and that, especially surprisingly, the supersaturation can be kept stable for hours. This allows the concentration of the β-lactam nucleus and/or the dissolved acylation agent to be strongly increased, so that the reaction proceeds more rapidly, with less degradation of the β-lactam antibiotic and/or the reactants and also with a higher yield of β-lactam antibiotic per amount of β-lactam nucleus employed and/or per amount of acylation agent employed. This also results in a higher production capacity.

In addition, it is known from literature, for example WO-A-92/01061, that a high yield of β-lactam antibiotic per amount of β-lactam nucleus can be obtained by applying a high molecular ratio between the acylation agent and the β-lactam nucleus. However, a drawback of applying a high molecular ratio between the acylation agent and the β-lactam nucleus is that large amounts of acylation agent are lost as a result of hydrolysis of the acylation agent (and possibly the β- lactam antibiotic). Consequently, a low synthesis/hydrolysis ratio (S/H), the molar ratio between synthesis product (β-lactam antibiotic) and hydrolysis product, is realized. Moreover, it has been found that working up the β-lactam antibiotic is often hampered by a relatively large amount of hydrolyzed acylation agent relative to β-lactam antibiotic being present in the reaction mixture obtained after the enzymatic acylation reaction, as a result of which a smaller amount of β-lactam antibiotic can be isolated.

For the purposes of the present invention, the yield of β-lactam antibiotic per amount of reactant (β-lactam nucleus or acylation agent) to be achieved in the acylation reaction means the (molar) amount of β-lactam antibiotic formed in the acylation reaction per (molar) amount of reactant employed.

For the purposes of the present invention, the solubility of a compound in a mixture means the dissolved concentration of the compound in the presence of all other components of the mixture, expressed in mmol/litre or mass %. The solubility is measured by dissolving the compound at constant pH and temperature and in the presence of all components of mixture. Thereafter, the solubility can be calculated from the amount of the compound dissolved on reaching equilibrium (saturated solution).

For the purposes of the present invention, a compound is supersaturated in a mixture when the dissolved concentration of that compound in the mixture is greater than the solubility. The supersaturation factor means the ratio between the two aforementioned solubilities (supersaturated divided by saturated). The supersaturation factor to be achieved and the time during which supersaturation is maintained depend on a number of factors such as the nature and concentration of the compound, the nature and concentrations of the other components in the mixture, the pH and the temperature. The supersaturation factor to be obtained depends largely on the compound involved and is preferably larger than 2, more particularly larger than 5.

The concentration of the dissolved β-lactam nucleus is expressed as the amount of dissolved β-lactam nucleus in moles per kg of liquid reaction mixture; the total concentration of dissolved and undissolved β-lactam nucleus is expressed as the amount of β-lactam nucleus in moles per kg of the total reaction mixture; the total reaction mixture may contain, besides the solution, a plurality of solids, for example β-lactam nucleus, β-lactam antibiotic, (hydrolyzed) acylation agent and immobilized enzyme. Similar definitions are applicable for the acylation agent and the β-lactam antibiotic.

A mixture in which the β-lactam nucleus or the acylation agent, respectively, is supersaturated can be obtained by means of for example a pH shift. To in that end, if necessary, a concentrated mixture can first be prepared as a slurry or a solution by dissolving β-lactam nucleus or acylation agent, respectively, present in solid form with the aid of for example a pH increase or a pH decrease, or a pH decrease, respectively. It is preferred for the β-lactam nucleus and/or the acylation agent to be dissolved in the mixture obtained. However, it is also possible for a portion of the β-lactam nucleus and/or the acylation agent to be still present in solid form. Subsequently, this slurry or solution can be subjected to a pH decrease or a pH increase, or a pH increase, respectively. In this way, a slurry or solution is obtained in which the β-lactam nucleus or acylation agent is supersaturated.

Any solid β-lactam nucleus present can be dissolved by for example decreasing the pH until a pH lower than 3, preferably lower than 2, in particular lower than 1 is reached; or by increasing the pH to a pH higher than 6, preferably higher than 7, in particular higher than 8. In practice, the final pH is preferably chosen such that the β-lactam nucleus goes only just completely into solution so that as concentrated a solution as possible is obtained. In practice, the concentrated solution will usually have a concentration of the β-lactam nucleus of at least 5 wt. %. The final pH will usually be lower than 10 and greater than 0.

Subsequently, a supersaturated solution can be obtained from a solution, whose pH may or may not have been decreased or increased, by increasing or decreasing the pH to a value between for example 3.0 and 9.0, preferably between 4.0 and 8.5, in particular between 4.5 and 8.0.

Any solid acylation agent present can be dissolved by for example decreasing the pH until a value lower than 8.0, preferably lower than 6.5, in particular lower than 5.0 is reached; preferably, the final pH is chosen such that the acylation agent is only just completely dissolved and thus as concentrated a solution as possible is obtained. In practice, the concentrated solution will have a concentration of the acylating agent of at least 5 wt. %. The final pH will usually be greater than 1.

A mixture supersaturated with for example the acylation agent can be obtained from a mixture, preferably a solution, whose pH may optionally have been reduced, by increasing the pH to a value greater than for example 4.5, preferably greater than 5.5, in particular greater than 6.0.

Another manner of obtaining a mixture in which the β-lactam nucleus and/or the acylation agent are/is supersaturated is for example by a temperature decrease, optionally after any solid β-lactam nucleus and/or solid acylation agent present have/has first at least partly been dissolved by a temperature increase or pH change.

Dissolution can be effected by for example a temperature increase until for example (virtually) all solid matter is in solution, for example to a temperature higher than 15° C., preferably higher than 20° C., in particular higher than 25° C. Subsequently, a supersaturated slurry or solution can be obtained from the obtained mixture by decreasing the temperature to a temperature lower than 20° C., preferably lower than 15° C., in particular lower than 10° C.

The supersaturated mixture preferably is prepared by changing the pH inasmuch as a higher supersaturation factor can then be achieved. In practice, a pH change and a temperature decrease will usually be applied simultaneously in the preparation of a supersaturated solution.

In a suitable embodiment of the process according to the invention first a mixture in which the β-lactam nucleus and/or the acylation agent are/is supersaturated is prepared, whereupon the acylation reaction is started by for example adding (immobilized) enzyme. The concentration of the reactants will decrease during the acylation reaction so that supersaturation will have gone by the end of the acylation reaction. In another suitable embodiment the acylation reaction is started with a portion of the β-lactam nucleus and/or the acylation agent, which may or may not be supersaturated, whereupon supersaturation is either maintained or brought about by adding to the reaction mixture, for example by titration, a concentrated mixture of the β-lactam nucleus and/or the acylation agent with a different pH or a higher temperature than the pH or temperature at which the acylation reaction is carried out. In practice, the β-lactam nucleus and the acylation agent may both be present in supersaturated condition during the acylation reaction, for example by metering into the acylation reactor a concentrated solution or slurry of the β-lactam nucleus (with a high pH or optionally with a low pH) and at the same time a concentrated solution or slurry of the acylation agent (with a low pH). In so doing, the pH can if desired be kept constant during the acylation reaction by for example titration.

The process according to the invention can very suitably be used in the preparation of cefaclor.

Cefaclor exhibits poor stability at high pH (>6.5) whilst the solubility of the corresponding β-lactam nucleus (7-amino-3-chloro-cef-3-em-4-carboxylic acid; 7-ACCA) is low at those pH values (about 6.0–6.5) at which degradation of cefaclor still is relatively low.

As a result, the yield of cefaclor was low at both relatively high and relatively low pH, so that a technically/commercially attractive process was not possible. The yield of cefaclor per amount of 7-ACCA employed and per amount of acylation agent employed could admittedly be improved by using for example naphthol as a complexing agent; the use of such toxic auxiliary materials in the preparation of antibiotics is, however, disadvantageous in that they need to be completely removed, which entails additional process steps, with a strongly negative effect on process economics. Surprisingly, it has been found that the process according to the invention allows an exceptionally high supersaturation factor (>10) to be achieved so that the acylation reaction can be carried out at a relatively low pH (6.0–6.5) whilst, yet, the concentration of the β-lactam nucleus is sufficiently high. Thus, it is now possible to prepare cefaclor in high yields through enzymatic acylation without using auxiliary materials so that a technically/commercially attractive process can be realized.

Another application of the process according to the invention lies in the preparation of for example ampicillin by acylation of 6-aminopenicillanic acid (6-APA) with the aid of D-phenyl glycine amide (FGA). Since 6-APA and ampicillin degrade relatively quickly at high concentration and at high pH it is important to have the acylation reaction proceed as rapidly as possible at as low a pH as possible. By for example increasing the pH of a mixture of 6-APA and FGA to a value between 7.0 and 8.0 and then immediately lowering it to a pH between 6.0 and 6.5 and then immediately initiating the enzymatic reaction it has been found possible to achieve, in a short period of time, a high yield of ampicillin per amount of 6-APA employed and per amount of acylation agent employed, with a relatively high concentration of 6-APA being present in the solution only very briefly and with degradation of ampicillin being kept low at the relatively low pH value. At the same time, hydrolysis of FGA to D-phenyl glycine (FG) is restricted.

The process according to the invention can also be applied with advantage in the enzymatic preparation of cephalexin through acylation of 7-aminodesacetoxycephalosporanic acid (7-ADCA) with the aid of D-phenyl glycine amide (FGA). The acylation reaction is usually carried out at a relatively high pH value, for example between 7.5 and 8.5, and is attended by (unwanted) hydrolysis of FGA into D-phenyl glycine (FG). The reaction can be accelerated, and hydrolysis of the acylation agent can be limited, by applying the process according to the invention, for example by first raising the pH of a mixture of FGA and 7-ADCA to for example a pH between 8.0 and 9.0 and then acidifying the mixture again to a pH between 6.5 and 8.5.

Another example of the process according to the invention is its application in the enzymatic preparation of amoxicillin from 6-APA and D-p-hydroxyphenyl glycine methyl ester (FGHM) and in the preparation of cefadroxil from 7-ADCA and FGHM. The solubility of FGHM is relatively low and decreases with increasing pH, whereas the solubility of 6-APA and 7-ADCA is also relatively low and decreases with decreasing pH. It has been found that subjecting a mixture of for example 6-APA or 7-ADCA and FGHM to a pH decrease to a value at which FGHM is virtually completely dissolved (for example a pH value between 5 and 6) and next to a pH increase to a value between for example 6 and 7.5 enables a supersaturation of FGHM by a factor of 3–5 to be achieved. Thus, the acylation reaction can be carried out at a somewhat higher pH, with a higher concentration of dissolved β-lactam nucleus, whilst the concentration of the acylation agent is also relatively high.

Another embodiment is to dissolve 7-ADCA to a relatively high concentration with a base to a pH between for example 8 and 9 and then adding a concentrated, acid solution of FGHM, in which process the pH decreases. In this embodiment, supersaturation of both 7-ADCA and FGHM can be achieved at the same time. The enzymatic reaction can be started after all reactants have been added. It is also possible to add (a portion of the) concentrated FGHM or 7-ADCA solution (or slurry) during the reaction.

Another example of the process according to the invention is its application in the enzymatic preparation of cefazolin from tetrazole-1-acetic acid and as a β-lactam nucleus 7-aminocephalosporanic acid (7-ACA) or 7-amino-3-(5-methyl-1,3,4-thiadiazole-2-yl-thiomethyl)-3-cef-em-4-carboxylic acid (7-ACA-MMTD). As the acylating agent does not contain an ax-amino group, a so-called thermodynamically controlled coupling reaction with the acid may be performed. The optimum pH for such thermodynamically controlled coupling reaction is preferably between 4.0 and 6.5. At this pH the solubility of the β-lactam nucleus is relatively low. It has appeared that the conversion in the coupling reaction can be strongly enlarged by adding a concentrated solution of the β-lactam nucleus with a relatively high pH (for instance between 7.0 and 9.0) to the enzymatic reaction mixture, while the pH of the reaction mixture is kept at a value between 4.0 and 6.5, e.g. by titration with an acid.

The process according to the invention can suitably be applied in the preparation of β-lactam antibiotics, for example cephalexin, ampicillin, cefaclor, amoxicillin, cephradine, cefadroxil, cefotaxime, cefazolin, cefprozil, loracarbef and cefaloglycin.

Any β-lactam nucleus can in principle be used, in particular a β-lactam nucleus with the general formula (1)

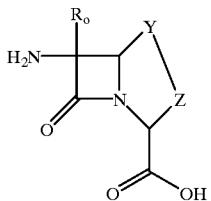

where $R_0$ represents H or an alkoxy group having 1–3 C atoms; Y represents $CH_2$, O, S or an oxidized form of sulphur; and Z represents

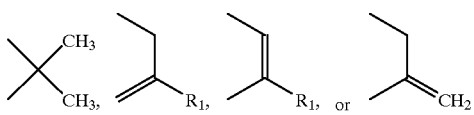

where $R_1$ represents for example H, OH, halogen, an alkoxy group having 1–5 C atoms, an alkyl group having 1–5 C atoms, a cycloalkyl group having 4–8 C atoms, an aryl or a heteroaryl group having 6–10 C atoms, in which the groups may or may not be substituted with for example an alkyl, an aryl, a carboxy or an alkoxy group having 1–8 C atoms; and where the carboxylic acid group may be an ester group if so desired.

Suitable examples of β-lactam nuclei that may be employed in the process according to the invention are penicillin derivatives, for example 6-aminopenicillanic acid (6-APA) and cephalosporic acid derivatives, for example a 7-aminocephalosporanic acid with or without a substituent at the 3-site, for example 7-aminocephalosporanic acid (7-ACA), 7-aminodesacetoxycephalosporanic acid (7-ADCA), 7-amino-3-chloro-cef-3-em-4-carboxylic acid (7-ACCA), 7-amino-3-(1-propenyl)-cef-3-em-4-carboxylic acid (7-PACA), 7-amino-3-(5-methyl-1,3,4-thiadiazole-2-yl-thiomethyl)cef-3-em-4-carboxylic acid (7-ACA-MMTD) and 7-amino-3-chloro-8-oxo-1-azabicyclo[4.2.0]oct-2-ene-2-carboxylic acid.

In the (enzymatic) acylation reaction, the acylation agent may be for instance a phenyl glycine in activated form, preferably a (primary, secondary or tertiary) amide or salt thereof, or a lower alkyl (1–4C) ester, for instance a methyl ester; suitable phenyl glycines are for example substituted and unsubstituted phenyl glycines, in particular phenyl glycine, β-hydroxyphenyl glycine, dihydrophenyl glycine. In addition α-substituted acetic acid derivatives and the corresponding amides and esters may be applied, for instance phenyl acetic acid, phenoxy acetic acid, tetrazole-1-acetic acid, mandelic acid or thienyl acetic acid.

In principle, any enzyme that is suitable as a catalyst in the coupling reaction can be used as the enzyme. Such enzymes include the enzymes collectively referred to as penicillin amidase or penicillin acylase. Such enzymes are described in for example J. G. Shewale et al., Process Biochemistry, August 1989, pp. 146–154 and in J. G. Shewale et all, Process Biochemistry International, June 1990, pp. 97–103. Examples of suitable enzymes are enzymes derived from Acetobacter, in particular *Acetobacter pasteurianum*, Aeromonas, Alcaligenes, in particular *Alcaligenes faecalis*, Aphanocladium, Bacillus sp., in particular *Bacillus megaterium*, Cephalosnorium, Escherichia, in particular *Escherichia coli*, Flavobacterium, Fusarium, in particular *Fusarium oxysporum* and *Fusarium solani*, Kluyvera, Mycoplana, Protaminobacter, Proteus, in particular *Proteus rettgari*, Pseudomonas and Xanthomonas, in particular *Xanthomonas citrii*.

Preferably an immobilized enzyme is used, since in that case the enzyme can be easily isolated and re-used.

Particularly suitable enzymes among the immobilized enzymes that are commercially available are for example the *Escherichia coli* enzyme from Boehringer Mannheim GmbH, which is commercially available under the name Enzygel$^R$, the immobilized Penicillin-G acylase from Recordati and the immobilized Penicillin-G acylase from Pharma Biotechnology Hannover. In addition, enzymes may also be utilized in crystalline form (CLEC's™).

The temperature at which the enzymatic acylation reaction is effected usually is below 40° C., preferably between −5 and 35° C. The pH at which the enzymatic acylation reaction is effected usually is between 3.0 and 9.5, preferably between 4.0 and 9.0. The optimum pH for a kinetically controlled coupling reaction is relatively high, for instance between 4.5 and 9.0, preferably between 5.5 and 8.5, in particular between 6.0 and 8.0. The optimum pH of a thermodynamically controlled coupling reaction generally is lower and lies for instance between 3.0 and 7.0, preferably between 4.0 and 6.5.

The reaction preferably is stopped almost completely when maximum conversion has virtually been achieved. A suitable embodiment for stopping the reaction is to lower the pH, preferably to a value between 4.0 and 6.3, in particular between 4.5 and 5.7. Another suitable embodiment is to lower the temperature of the reaction mixture on attaining the maximum conversion. A combination of the two embodiments is possible also.

Once the reaction has been stopped on attaining the maximum conversion, the reaction mixture usually is present in the form of a suspension comprising a plurality of solids, for example the antibiotic, D-phenyl glycine and, possibly, immobilized enzyme. The immobilized enzyme preferably is recovered in the interest of process economics. This can suitably be accomplished by for example by filtering the reaction mixture on a sieve, while stirring, the stirrer's direction of rotation being chosen so that the suspension is pumped upwards at the centre of the stirrer. Subsequently, valuable components such as the antibiotic and FG can be recovered by means of for example a pH change.

For the purposes of the invention, a pH change can be brought about by adding an acid. Suitable acids are for example mineral acids, in particular sulphuric acid, hydrochloric acid or nitric acid and carboxylic acids, for example acetic acid, oxalic acid and citric acid. A pH increase can be brought about by for example adding a base. Suitable bases are for example inorganic bases, in particular ammonium hydroxide, potassium hydroxide or sodium hydroxide, and organic bases, for example triethyl amine and FGA. Preferably, ammonium hydroxide is used.

The enzymatic acylation reaction and the measures mentioned, for example the preparation of the supersaturated mixtures, can be effected in water. If desired, the reaction mixture may also contain an organic solvent or a mixture of organic solvents, preferably less than 30 vol. %. Examples of suitable organic solvents are alcohols having 1–7 C atoms, for example a monoalcohol, in particular methanol or ethanol; a diol, in particular ethylene glycol, or a triol, in particular glycerol.

The molar ratio of acylation agent to β-lactam nucleus, i.e. the total amount of acylation agent added, divided by the total amount of β-lactam nucleus added, expressed in moles, is less than 2.5. It is preferred for the molar ratio to be between 0.5 and 2.0, in particular between 0.7 and 1.8.

The enzymatic acylation reaction is preferably carried out as a batch process. If desired, the reaction can also be carried out continuously.

The invention will be further elucidated by means of the following examples, without however being restricted thereto.

Abbreviations

7-ACCA: 7-amino-3-chloro-cef-3-em-4-carboxylic acid
7-ADCA: 7-aminodesacetoxycephalosporanic acid
6-APA: 6-amino-penicillanic acid
10 AMPI: ampicillin
CCl: cefaclor
CEX: cephalexin
FG: D-phenyl glycine
FGA: D-phenyl glycine amide
FGH: D-p-hydroxyphenyl glycine
FGHM: D-p-hydroxyphenyl glycine methyl ester Assemblase™ is an immobilized Escherichia coli penicillin acylase from E. coli ATCC 1105 as described in WO-A-97/04086. The immobilization is effected as set out in EP-A-222462, with gelatin and chitosan being used as gelating agents and glutaraldehyde as crosslinking agent.

The ultimate activity of the Escherichia coli penicillin acylase is determined by the amount of enzyme added to the activated globules and amounted to 3 ASU/g of dry weight, 1 ASU (Amoxicillin Synthesis Unit) being defined as the amount of enzyme capable of producing 1 g of Amoxicillin.3H$_2$O from 6-APA and FGHM per hour (at 20° C.; 6.5% 6-APA and 6.5% FGHM).

Comparative Example 1

Synthesis of Cefaclor (7-ACCA not Supersaturated)

An enzyme reactor (1.5 l, diameter 11 cm), fitted with a 175 μm mesh sieve bottom, was filled with 100 g of net-wet Assemblase™.

A preparation reactor (1.2 l) was filled with 75.4 g of FGA (0.500 mole), 4.0 g of sodium bisulphite, 700 g of water, 6.6 g of 4N H$_2$SO$_4$ and 72.1 g of 7-ACCA (0.300 mol). This mixture was stirred at T=10° C.; the pH was 7.5. Subsequently, the mixture was transferred into the enzyme reactor with the aid of 118 ml of water (T=10° C.).

The stirrer in the enzyme reactor was switched on at t=0. The temperature was kept at 10° C. The pH was kept at 7.5 by titration with 4N H$_2$SO$_4$. At t=48 minutes the enzyme reactor contained approx.:

215 mmol CCl (conversion=72%)
70 mmol 7-ACCA
175 mmol FGA
95 mmol FG

At t=81 minutes the enzyme reactor contained approx.:

212 mmol CCl (conversion=71%)
61 mmol 7-ACCA
83 mmol FGA
182 mmol FG

Thereafter, the amount of CCl decreased.

EXAMPLE I

Synthesis of Cefaclor (7-ACCA Supersaturated)

An enzyme reactor (1.5 l, diameter 11 cm), fitted with a 175 μm mesh sieve bottom, was filled with 300 g of net-wet Assemblase™.

A preparation reactor (1.2 l) was filled with 86.6 g of 7-ACCA (0.360 mol), 67.8 g of FGA (0.450 mol), 4.0 g of sodium bisulphite and 402 g of water. This mixture was stirred for 5 minutes at T=10° C.; the pH was 7.4.

The pH was brought to 8.0, while stirring, with the aid of 16.8 g of concentrated ammonium hydroxide. Subsequently, the pH was lowered from 8.0 to 6.4 by metering in 73.8 ml of 4N H$_2$SO$_4$ in 20 minutes. Next, at t=0, the mixture was transferred from the preparation reactor to the enzyme reactor with the aid of 140 ml of water (T=10° C.)

The stirrer in the enzyme reactor was switched on at t=0; T=10° C. The pH was kept at 6.4 by titration with 4N H2SO$_4$. After 7 hours, 66.0 ml of acid had been added. The reactor now contained:

300 mmol CCl (conversion=83%)
55 mmol 7-ACCA
100 mmol FGA
45 mmol FG

EXAMPLE II

Synthesis of Cefaclor (7-ACCA Supersaturated and 7-ACCA Being Metered in During the Enzymatic Reaction)

An enzyme reactor (1.5 l, diameter 11 cm), fitted with a 175 μm mesh sieve bottom, was filled with 150 g of net-wet Assemblase™.

A preparation reactor (1.2 l) was filled with 48.1 g of 7-ACCA (0.200 mol), 75.4 g of FGA (0.500 mol), 4.0 g of sodium bisulphite and 175 g of water. This mixture was stirred for 5 minutes at T=10° C.; the pH was 7.43.

The pH was brought to 9.0, while stirring, with the aid of 15.5 g of concentrated ammonium hydroxide. Subsequently, the pH was lowered from 9.0 to 6.4 by metering in 80.6 ml of 6N H$_2$SO$_4$ in 45 minutes. Next, at t=0, the mixture was transferred from the preparation reactor to the enzyme reactor with the aid of 40 g of water (T=10° C.).

The stirrer in the enzyme reactor was switched on at t=0. The temperature was kept at T=10° C. 244 g (0.200 mol) of 7-ACCA solution were metered in at a constant rate in 109 minutes. The solution had been freshly prepared by suspending 48.1 g of 7-ACCA (0.200 mol) in 183 g of water at T=3° C. and raising the pH to 8.2 with the aid of 13.2 concentrated $NH_3$, in which process all 7-ACCA dissolved. From t=0 onwards, the pH in the enzyme reactor was kept at 6.4 by titration with 6N $H_2SO_4$. At t=350 minutes the enzyme reactor contained:

350 mmol CCl (conversion=88%)
45 mmol 7-ACCA
80 mmol FGA
65 mmol FG

At t=400 minutes the amount of Cefaclor was maximum and the pH was lowered to 5.0 by adding 6N $H_2SO_4$. The enzyme reactor now contained:

370 mmol CCl (conversion=92%)
25 mmol 7-ACCA
40 mmol FGA
85 mmol FG

Comparative Experiment B

Synthesis of Ampicillin (6-APA not Supersaturated)

First a solution of FGA. 1/2 $H_2SO_4$ was prepared. 301.6 g of FGA (2.00 mol) were suspended in 650 g of water at T=5° C. 102.1 g of 96% $H_2SO_4$ (1.00 mol) were added dropwise while stirring, with the temperature being kept at T<25° C. by means of cooling.

Next the enzymatic condensation was performed. An enzyme reactor (1.5 l, diameter 11 cm), fitted with a 175 μm mesh sieve bottom, was filled with 300 g of net-wet Assemblase™.

A preparation reactor (1.2 l) was filled with 131.6 g of 6-APA (0.600 mol), 30.2 g of FGA (0.200 mol) and 400 ml of water (T=10° C.). This mixture was stirred for 15 minutes at T=10° C. and subsequently, at t=0 transferred into the enzyme reactor with the aid of 100 ml of water (T=10° C.)

The stirrer in the enzyme reactor was switched on at t=0. 423.7 g (0.800 mol) of FGA. $1/2H_2SO_4$ were added to the solution at a constant rate in 283 minutes, with the temperature being kept at 10° C. The pH was 6.3 From t=328 minutes onwards, the pH was kept at 6.3 by titration with 6N $H_2SO_4$.

At t=540 minutes the amount of Ampicillin was maximum and the pH was lowered to 5.6 by adding 6N $H_2SO_4$. The enzyme reactor now contained:

575 mmol AMPI (=96% relative to the amount of 6-APA employed)
15 mmol 6-APA
50 mmol FGA
365 mmol FG

EXAMPLE III

Synthesis of Ampicillin (6-APA Supersaturated)

An enzyme reactor (1.5 l, diameter 11 cm), fitted with a 175 μm mesh sieve bottom, was filled with 300 g of net-wet Assemblase™.

A preparation reactor (1.2 l) was filled with 550 ml of water (T=10° C.), 138.8 g (0.920 mol) of FGA and 131.6 g (0.600 mol) of 6-APA. After 5 minutes at 10° C. a clear solution obtained with a pH value of 7.4. Subsequently, the pH was brought to 6.5 with 96% $H_2SO_4$ (ca. 16 g) and after stirring for 5 minutes at 10° C. the solution was transferred to the enzyme reactor at t=0 with the aid 100 ml of water (T=10° C.).

At t=0 the temperature was 10° C. and the pH =6.3. During the enzyme reaction the pH was kept at 6.3 by titration with 6N $H_2SO_4$. At t=300 minutes the amount of AMPI was maximum and the pH was lowered to 5.6 by adding 6N $H_2SO_4$.

The enzyme reactor now contained:

575 mmol AMPI (=96% relative to the amount of 6-APA employed)
15 mmol of 6-APA
40 mmol of FGA
295 mmol PG

Comparative Example C

Synthesis of Cephalexin (7-ADCA not Supersaturated)

An enzyme reactor (1.5 l, diameter 11 cm), fitted with a 175 μm mesh sieve bottom, was filled with 75 g of net-wet Assemblase™.

A preparation reactor (1.2 l) was filled with 668 g of water (T=4° C.), 4.0 g of sodium bisulphite, 130.3 g of 7-ADCA (0.600 mol) and 75.4 g of FGA (0.500 mol). 7.8 g of concentrated ammonium hydroxide were added, whereupon the suspension was stirred for 15 minutes at T=4° C. The pH was 7.8.

Subsequently, at t=0, the suspension was transferred into the enzyme reactor with the aid of 50 ml of water (T=4° C.). The stirrer in the enzyme reactor was switched on at t=0. The temperature was kept at T=4° C. all the time. All 7-ADCA had dissolved after approximately 75 minutes; thereafter, a clear solution, apart from solid Assemblase™, was present. After 210 minutes the pH had risen to 8.6.

The reactor now contained:

393 mmol CEX (conversion=66%; S/H=6.1)
200 mmol 7-ADCA
64 mmol FG
33 mmol FGA.

EXAMPLE IV

Synthesis of Cephalexin (7-ADCA Supersaturated)

An enzyme reactor (1.5 l, diameter 11 cm), fitted with a 175 μm mesh sieve bottom, was filled with 75 g of net-wet Assemblase™.

A preparation reactor (1.2 l) was filled with 600 ml of water (T=4° C.), 4.0 g of sodium bisulphite, 130.3 g of 7-ADCA (0.600 mol) and 90.5 g of FGA (0.600 mol). The suspension was stirred for 15 minutes at T=4° C. The pH was 7.6.

The pH was brought to 8.6, with stirring, using 43.8 g of concentrated ammonium hydroxide. Stirring was effected for 5 minutes at T=4° C. Subsequently, 21.2 g of concentrated $H_2SO_4$ were added. The clear solution was stirred for 15 minutes at T=4° C. The pH was 7.4.

Subsequently, at t=0, the suspension was transferred into the enzyme reactor with the aid of 50 ml of water (T=4° C.). The stirrer in the enzyme reactor as switched on at t=0. The temperature was kept at T=4° C. all the time. At t=90 minutes the pH had risen to 8.05. 5.5 g of concentrated $H_2SO_4$ were added, causing the pH to decrease to 7.75. A clear solution, apart from solid Assemblase™, was present throughout the enzyme reaction.

After 340 minutes the pH had risen to 8.5.
The reactor now contained:
  445 mmol CEX (conversion=74%; S/H=7.2)
  146 mmol 7-ADCA
  62 mmol FG
  80 mmol FGA.

EXAMPLE V

Synthesis of Cephalexin (7-ADCA Supersaturated)

An enzyme reactor (1.5 l, diameter 11 cm), fitted with a 175 µm mesh sieve bottom, was filled with 75 g of net-wet Assemblase™.

A preparation reactor (1.2 l) was filled with 500 ml of water (T=4° C.), 4.0 g of sodium bisulphite, 162.9 g of 7-ADCA (0.750 mol) and 113.1 g of FGA (0.750 mol). The suspension was stirred for 15 minutes at T=4° C. The pH was 7.6.

The pH was brought to 8.7, with stirring, using 55.6 g of concentrated ammonium hydroxide. Stirring was effected for 5 minutes at T=4° C. Subsequently, 9.6 g of concentrated $H_2SO_4$ were added. The clear solution was stirred for 15 minutes at T=4° C. The pH was 8.0.

Subsequently, at t=0, the suspension was transferred into the enzyme reactor with the aid of 50 ml of water (T=4° C.). The stirrer in the enzyme reactor was switched on at t=0. The temperature was kept at T=4° C. all the time. After 60 minutes the pH had risen to 8.3. The pH was now kept at 8.3 by titration with concentrated $H_2SO_4$.

At t=300 minutes a total of 23.4 g of concentrated $H_2SO_4$ had been titrated. At this point titration was stopped; at t=450 minutes the pH had risen to 8.7.

A clear solution, apart from solid Assemblase™, was present throughout the enzyme reaction.

At t=450 minutes the reactor contained:
  545 mmol CEX (conversion=73%; S/H=8.5)
  195 mmol 7-ADCA
  64 mmol FG
  129 mmol FGA.

Comparative Experiment D

Synthesis of Cefadroxil (neither 7-ADCA nor FGHM Supersaturated)

An enzyme reactor (1.5 l, diameter 11 cm), fitted with a 175 µm mesh sieve bottom, was filled with 300 g of net-wet Assemblase™.

A preparation reactor (1.2 l) was filled with 63.7 ml of 7-ADCA (0.293 mol), 107.1 g of FGHM (0.590 mol), 4.0 g of sodium bisulphite and 440 g of water. This mixture was stirred for 5 minutes at T=10° C. with the pH being kept at 7.0 with the aid of 7.5 g of concentrated ammonium hydroxide.

At t=0, the suspension was transferred from the preparation reactor into the enzyme reactor with the aid of 50 ml of water (T=10° C.). The stirrer in the enzyme reactor was switched on at t=0. The temperature was kept at T=10° C.; the pH remained constant at 7.0 (no titration).

After 380 minutes the enzyme reactor contained:
  68 mmol Cefadroxil (conversion=23%; S/H=0.67)
  222 mmol 7-ADCA
  420 mmol FGHM
  101 mmol FGH

EXAMPLE VI

Synthesis of Cefadroxil (both FGHM and 7-ADCA Supersaturated)

An enzyme reactor (1.5 l, diameter 11 cm), fitted with a 175 µm mesh sieve bottom, was filled with 270 g of net-wet Assemblase™.

A preparation reactor (1.2 l) was filled with 97.7 ml of 7-ADCA (0.448 mol), 4.0 g of sodium bisulphite and 250 g of water (T=10° C.). The suspension was stirred for 5 minutes at T=10° C. Subsequently, the pH was brought to 8.1 with the aid of 40.3 g of $NH_3$, in which process a clear solution evolved (T=10° C.).

A second preparation reactor was filled with 98.5 g of FGHM (0.538 mol), 60 g of water (T=10° C.) and 105.1 g of 6N $H_2SO_4$ solution. This solution was brought to T=10° C.; pH=2.3.

The 7-ADCA solution from the first preparation reactor was transferred to the enzyme reactor with the aid of 20 ml of water (T=10° C.). The stirrer in the enzyme reactor was switched on. From t=0 the FGHM solution from the second preparation reactor was metered into the enzyme reactor at a constant rate in 120 minutes. The temperature was kept at T=10° C.

After 30 minutes the pH had decreased from 8.1 to 6.8. Next, the pH was maintained at 6.8 by titration with a concentrated ammonium hydroxide. At t=120 minutes, 8.3 g of concentrated ammonium hydroxide had been added. Titration was stopped; the pH continued to be 6.8.

After 420 minutes the enzyme reactor contained:
  390 mmol Cefadroxil (conversion 87%; S/H=4.0
  50mmol 7-ADCA
  44 mmol FGHM
  97 mmol FGH

What is claimed is:

1. Process for the preparation of a β-lactam antibiotic in which a β-lactam nucleus is subjected to an enzymatic acylation reaction with the aid of an acylation agent at a molar ratio of acylation agent/β-lactam nucleus of less than 2.5, wherein the acylation agent and/or the β-lactam nucleus are/is supersaturated in the reaction mixture during at least part of the acylation reaction.

2. Process according to claim 1, in which the acylation agent and/or the β-lactam nucleus are/is supersaturated in the reaction mixture at the beginning of the acylation reaction.

3. Process according to claim 1, in which a concentrated slurry or solution of the β-lactam nucleus and/or the acylation agent with a different pH or a higher temperature than the pH or temperature at which the acylation reaction is carried out is added to the reaction mixture during the acylation reaction.

4. Process according to claim 1 in which the β-lactam nucleus is supersaturated in the reaction mixture.

5. Process according to claim 4 in which a mixture in which the β-lactam nucleus is dissolved is subjected to a pH decrease or a pH increase until a pH between 3.0 and 9.0 is reached.

6. Process according to claim 5 in which the pH decrease or pH increase is effected until a pH between 4.0 and 8.5 is reached.

7. Process according to claim 1 in which the acylation agent is supersaturated in the reaction mixture.

8. Process according to claim 7 in which a mixture in which the acylation agent is dissolved is subjected to a pH increase.

9. Process according to claim 8 in which the pH is increased to a pH higher than 5.5.

10. Process according to claim 9 in which the pH is increased to a pH higher than 6.

11. Process according to claim 4 in which a mixture containing dissolved β-lactam nucleus and/or acylation agent is subjected to a temperature decrease.

12. Process according to claim 11 in which the temperature is decreased to a temperature below 15° C.

13. Process according to claim 12 in which the temperature is decreased to a temperature below 10° C.

14. Process according to claim 7 in which the methyl ester of p-hydroxyphenyl glycine is used as acylation agent.

15. Process according to claim 1 in which an amide is used as acylation agent.

16. Process according to claim 1 in which 7-aminodesacetoxycephalosporanic acid (7-ADCA), 7-amino-3-chloro-cef-3-em-4-carboxylic acid (7-ACCA), 6-aminopenicillanic acid (6-APA), 7-aminocefalosporanic acid (7-ACA), 7-amino-3-(1-propenyl)-cef-3-em-4-carboxylic acid (7-PACA), 7-amino-3-(5-methyl-1,3,4-thiadiazole- 2-yl-thiomethyl)-cef-3-em-4-carboxylic acid (7-ACA-MMTD) or 7-amino-3-chloro-8-oxo-1-azabicyclo [4.2.0]oct-2-ene-2-carboxylic acid is used as β-lactam nucleus.

* * * * *